United States Patent [19]

Baumann et al.

[11] Patent Number: 5,753,594
[45] Date of Patent: May 19, 1998

[54] 3-HALO-3-HETARYLCARBOXYLIC ACID DERIVATIVES, AND PROCESSES AND INTERMEDIATES FOR THEIR PREPARATION

[75] Inventors: Ernst Baumann, Dudenhofen; Albrecht Harreus, Ludwigshafen; Matthias Bratz, Speyer; Joachim Rheinheimer; Uwe Josef Vogelbacher, both of Ludwigshafen; Hans Theobald; Matthias Gerber, both of Limburgerhof; Helmut Walter, Obrigheim; Karl-Otto Westphalen, Speyer; Wilhelm Rademacher, Limburgerhof, all of Germany

[73] Assignee: BASF Aktiengesellschaft, Ludwigshafen, Germany

[21] Appl. No.: 530,251

[22] PCT Filed: Apr. 13, 1994

[86] PCT No.: PCT/EP94/01140
§ 371 Date: Dec. 1, 1995
§ 102(e) Date: Dec. 1, 1995

[87] PCT Pub. No.: WO94/25455
PCT Pub. Date: Nov. 10, 1994

[30] Foreign Application Priority Data

Apr. 23, 1993 [DE] Germany .................. 43 13 411.4

[51] Int. Cl.⁶ .................. C07D 239/02; A01N 43/54
[52] U.S. Cl. .................. 504/239; 504/242; 504/243; 544/302; 544/314; 544/318; 544/319; 544/334
[58] Field of Search .................. 544/334, 302, 544/319, 318, 315, 314; 504/239, 242, 243

[56] References Cited

U.S. PATENT DOCUMENTS

| | | | |
|---|---|---|---|
| 4,968,340 | 11/1990 | Kaku et al. | 71/92 |
| 5,087,289 | 2/1992 | Kaku et al. | 71/93 |
| 5,139,563 | 8/1992 | Astles et al. | |
| 5,178,663 | 1/1993 | Harada et al. | |
| 5,270,289 | 12/1993 | Harde et al. | |
| 5,326,744 | 7/1994 | Rheinheimer et al. | |
| 5,561,148 | 10/1996 | Gante et al. | 514/376 |
| 5,661,106 | 8/1997 | Baumann et al. | 504/239 |

FOREIGN PATENT DOCUMENTS

| | | |
|---|---|---|
| 347 811 | 12/1989 | European Pat. Off. |
| 400 741 | 12/1990 | European Pat. Off. |
| 409 368 | 1/1991 | European Pat. Off. |
| 481 512 | 4/1992 | European Pat. Off. |
| 517 215 | 9/1992 | European Pat. Off. |
| 548 710 | 6/1993 | European Pat. Off. |
| 40 35 758 | 5/1992 | Germany. |

*Primary Examiner*—Mukund J. Shah
*Assistant Examiner*—Sabiha N. Qazi
*Attorney, Agent, or Firm*—Keil & Weinkauf

[57] ABSTRACT

3-Halo-3-hetarylcarboxylic acid derivatives having the formula I

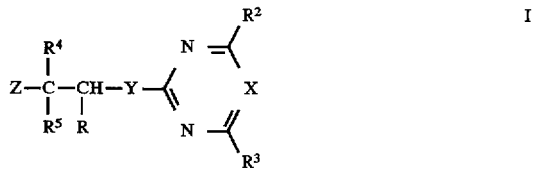

in which R is a formyl group, a group $CO_2H$ or a radical which can be hydrolyzed to COOH, and the remaining substituents have the following meanings:

$R^2$ and $R^3$ are halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

X is nitrogen or $CR^{13}$, where $R^{13}$ is hydrogen or together with $R^3$ forms an alkylene or alkenylene chain in which in each case one methylene group is replaced by oxygen;

$R^4$ is an unsubstituted or substituted five- or six-membered heteroaromatic ring which contains one to three nitrogen atoms and/or one sulfur or oxygen atom;

$R^5$ is hydrogen, substituted or unsubstituted alkyl, alkenyl, alkynyl, cycloalkyl or phenyl;

Y is sulfur, oxygen or a single bond; and

Z is halogen.

The derivatives I having herbicidal and plant-growth regulating properties.

11 Claims, No Drawings

3-HALO-3-HETARYLCARBOXYLIC ACID DERIVATIVES, AND PROCESSES AND INTERMEDIATES FOR THEIR PREPARATION

The present invention relates to 3-halo-3-hetarylcarboxylic acid derivatives of the general formula I

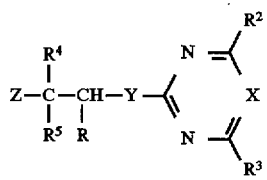

in which R is a formyl group, a group $CO_2H$ or a radical which can be hydrolyzed to COOH, and the remaining substituents have the following meanings:

$R^2$ is halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

X is nitrogen or $CR^{13}$, where $R^{13}$ is hydrogen or together with $R^3$ forms a 3- to 4-membered alkylene or alkenylene chain in which in each case one methylene group is replaced by oxygen;

$R^3$ is halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, or $R^3$ is linked to $R^{13}$ as mentioned above to form a 5- or 6-membered ring;

$R^4$ is a five- or six-membered heteroaromatic ring which contains one to three nitrogen atoms and/or one sulfur or oxygen atom and which can have attached to it one or more of the following radicals: halogen, nitro, cyano, hydroxyl, mercapto, amino, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino, di-$C_1$–$C_4$-alkylamino, $C_1$–$C_4$-alkylcarbonyl, $C_1$–$C_4$-alkoxycarbonyl or phenyl;

$R^5$ is hydrogen, $C_1$–$C_4$-alkyl, $C_3$–$C_6$-alkenyl, $C_3$–$C_6$-alkynyl, $C_3$–$C_8$-cycloalkyl, $C_1$–$C_4$-haloalkyl, $C_1$–$C_4$-alkoxyalkyl, $C_1$–$C_4$-alkylthioalkyl or phenyl;

Y is sulfur or oxygen or a single bond; and

Z is halogen.

Similar carboxylic acid derivatives, amongst others also 3-halo derivatives, are described in the literature, for example in EP-A 347 811, EP-A 400 741, EP-A 409 368, EP-A 481 512, EP-A 517 215 and in the earlier German Application P 41 42 570 (EP-A-548 710), but none of them have a hetaryl radical attached to them in the 3-position.

The biological action and selectivity of the known compounds is not always satisfactory.

It was an object of the invention to provide compounds with an improved selectivity to crop plants and/or better herbicidal or bioregulatory action.

We have found that this object is achieved by the 3-halo-3-hetarylcarboxylic acid derivatives defined at the outset, which have outstanding herbicidal and plant-growth-regulating properties.

The compounds according to the invention are synthesized starting from the epoxides IV, which are obtained from the aldehydes or ketones II or the olefins III in a generally known manner, for example as described by J. March, Advanced Organic Chemistry, 2nd ed., 1983, p. 862 and p. 750:

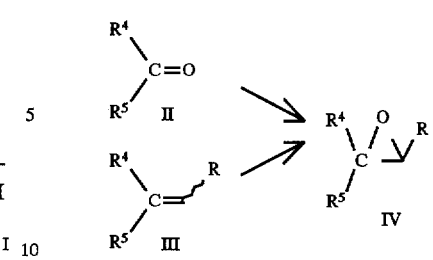

3-Halo-3-hetarylcarboxylic acid derivatives of the formula VI can be prepared by reacting the epoxides of the formula IV (for example where $R=COOR^9$) with halogen derivatives MZ of the formula V where Z has the meaning given in claim 1 and M is hydrogen, an alkali metal cation or the equivalent of an alkaline earth metal cation:

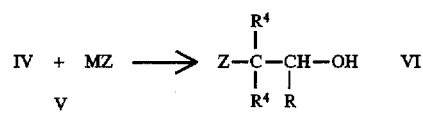

The reaction can also be carried out in the presence of a diluent. All solvents which are inert to the reagents used may be used for this purpose.

Examples of such solvents or diluents are water, aliphatic, alicyclic and aromatic hydrocarbons, all of which may be chlorinated, such as, for example, hexane, cyclohexane, petroleum ether, ligroin, benzene, toluene, xylene, methylene chloride, chloroform, carbon tetrachloride, ethylene chloride and trichloroethylene, ethers, such as, for example, diisopropyl ether, dibutyl ether, propylene oxide, dioxane and tetrahydrofuran, ketones, such as, for example, acetone, methyl ethyl ketone, methyl isopropyl ketone and methyl isobutyl ketone, nitriles, such as, for example, acetonitrile and propionitrile, alcohols, such as, for example, methanol, ethanol, isopropanol, butanol and ethylene glycol, esters, such as, for example, ethyl acetate and amyl acetate, acid amides, such as, for example, dimethylformamide and dimethylacetamide, sulfoxides and sulfones, such as, for example, dimethyl sulfoxide and sulfolane, and bases, such as, for example, pyridine.

The reaction is preferably carried out at from 0° C. to the boiling point of the solvent or solvent mixture.

The presence of a reaction catalyst may be advantageous. Suitable catalysts are organic acids and inorganic acids, and also Lewis acids. Examples are, inter alia, sulfuric acid, hydrochloric acid, trifluoroacetic acid, boron trifluoride etherate and titanium(IV) halides.

The compounds according to the invention where Y is oxygen and the remaining substituents have the meanings given under the general formula I can be prepared for example in such a way that the 3-halo-3-hetarylcarboxylic acid derivatives of the general formula VI are reacted with compounds of the general formula VII

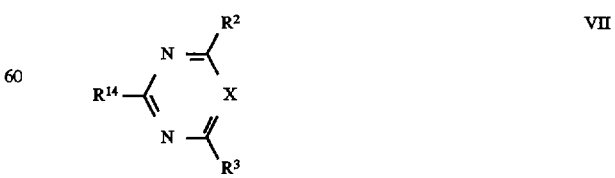

where $R^{14}$ is halogen or $R^{15}SO_2$—, $R^{15}$ being $C_1$–$C_4$-alkyl, $C_1$–$C_4$-haloalkyl or phenyl. The reaction is preferably carried out in one of the abovementioned inert diluents with the addition of a suitable base, i.e. a base which is capable of deprotonating the compound VI, at from room temperature to the boiling point of the solvent.

The base may be an alkali metal hydride or alkaline earth metal hydride, such as sodium hydride, potassium hydride or calcium hydride, a carbonate, i.e. alkali metal carbonate, such as sodium carbonate or potassium carbonate, an alkali metal hydroxide, such as sodium hydroxide or potassium hydroxide, an organometal compound, such as butyllithium, or an alkali metal amide, such as lithium diisopropylamide.

The compounds according to the invention where Y is sulfur and the remaining substituents have the meanings given under formula I can be prepared for example in such a manner that 3-halo-3-hetarylcarboxylic acid derivatives of the general formula VIII

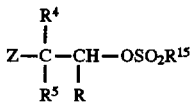
VIII which can be obtained in a known manner from compounds of the general formula VI and where the substituents have the meanings given above are reacted with compounds of the general formula IX

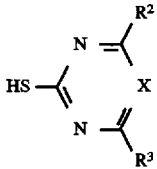
IX where $R^2$, $R^3$ and X have the meanings given under the general formula I.

The reaction preferably takes place in one of the above-mentioned inert diluents with the addition of a suitable base, i.e. a base which is capable of deprotonating the intermediate IX, at from room temperature to the boiling point of the solvent.

In addition to the abovementioned bases, organic bases, such as triethylamine, pyridine, imidazole or diazabicycloundecene, may also be used.

Compounds of the formula I can also be prepared by starting from the corresponding carboxylic acids, ie. compounds of the formula I where R is COOH, and first converting them in a customary manner into an activated form, such as a halide, an anhydride or an imidazolide, and then reacting this activated form with a suitable hydroxyl compound $HOR^9$. This reaction can be carried out in the customary solvents and is advantageously effected in the presence of a base, suitable bases being those mentioned above.

These two steps can also be simplified, for example by allowing the carboxylic acid to act on the hydroxyl compound in the presence of a dehydrating agent, such as a carbodiimide.

Moreover, compounds of the formula I can also be prepared by starting from the salts of the corresponding carboxylic acids, i.e. for example from compounds of the formula I in which R is a group $COR^1$ and $R^1$ is OM, it being possible for M to be, for example, an alkali metal cation or the equivalent of an alkaline earth metal cation. These salts can be reacted with many compounds of the formula $R^1$—A, A being a customary nucleofugic leaving group, for example halogen, such as chlorine, bromine, iodine, or aryl- or alkylsulfonyl which is unsubstituted or substituted by halogen, alkyl or haloalkyl, such as, for example, toluene-sulfonyl and methylsulfonyl, or another equivalent leaving group. Those compounds of the formula $R^1$—A having a reactive substituent A which are not already known can be obtained readily in a conventional manner known in the art. This reaction can be carried out in the customary solvents and is advantageously carried out in the presence of a base, suitable bases being those mentioned above.

The radical R in formula I can be varied greatly. For example, R is a group

in which $R^1$ has the following meanings:
a) hydrogen;
b) a succinylimidoxy group;
c) a 5-membered heteroaromatic ring, such as pyrrolyl, pyrazolyl, imidazolyl and triazolyl, which is linked via a nitrogen atom and which can have attached to it one or two halogen atoms, in particular fluorine and chlorine, and/or one or two of the following radicals:

$C_1$–$C_4$-alkyl, such as methyl, ethyl, 1-propyl, 2-propyl, 2-methyl-2-propyl, 2-methyl-1-propyl, 1-butyl, 2-butyl;

$C_1$–$C_4$-haloalkyl, in particular $C_1$–$C_2$-haloalkyl, such as, for example, fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl and pentafluoroethyl;

$C_1$–$C_4$-haloalkoxy, in particular $C_1$–$C_2$-haloalkoxy, such as difluoromethoxy, trifluoromethoxy, chlordifluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, in particular trifluoromethoxy;

$C_1$–$C_4$-alkoxy, such as methoxy, ethoxy, propoxy, 1-methylethoxy, butoxy, 1-methylpropoxy, 2-methylpropoxy, 1,1-dimethylethoxy, in particular methoxy, ethoxy, 1-methylethoxy;

$C_1$–$C_4$-alkylthio, such as methylthio, ethylthio, propylthio, 1-methylethylthio, butylthio, 1-methylpropylthio, 2-methylpropylthio, 1,1-dimethylethylthio, in particular methylthio and ethylthio;

d) $R^1$ is furthermore a radical —$(O)_m$—$NR^6R^7$ where m is 0 or 1 and $R^6$ and $R^7$ can be identical or different and have the following meanings:

hydrogen;

$C_1$–$C_8$-alkyl, in particular $C_1$–$C_4$-alkyl, as mentioned above;

$C_3$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2- dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl and 3-methyl-2-pentenyl;

$C_3$–$C_6$-alkynyl, such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably 2-propynyl, 2-butynyl, 1-methyl-2-propynyl and 1-methyl-2-butynyl, in particular 2-propynyl;

$C_3$–$C_8$-cycloalkyl, such as cyclopropyl, cyclobutyl, cyclopentyl, cyclohexyl, cyclohepthyl and cyclooctyl, it being possible for these alkyl, cycloalkyl, alkenyl and alkynyl groups to have attached to them in each case one to five, in particular one to three, halogen atoms, preferably fluorine or chlorine, and/or one or two of the following groups:

$C_1$–$C_4$-alkyl, $C_1$–$C_4$-alkoxy, $C_1$–$C_4$-alkylthio, $C_1$–$C_4$-haloalkoxy, as mentioned above, $C_3$–$C_6$-alkenyloxy, $C_3$–$C_6$-alkenylthio, $C_3$–$C_6$-alkynyloxy, $C_3$–$C_6$-alkynylthio, the alkenyl and alkynyl moieties in these radicals preferably having the abovementioned meanings;

$C_1$–$C_4$-alkylcarbonyl, such as, in particular, methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl;

$C_1$–$C_4$-alkoxycarbonyl, such as methoxycarbonyl, ethoxycarbonyl, propyloxycarbonyl, 1-methylethoxycarbonyl, butyloxycarbonyl, 1-methylpropyloxycarbonyl, 2-methylpropyloxycarbonyl, 1,1-dimethylethoxycarbonyl;

$C_3$–$C_6$-alkenylcarbonyl, $C_3$–$C_6$-alkynylcarbonyl, $C_3$–$C_6$-alkenyloxycarbonyl and $C_3$–$C_6$-alkynyloxycarbonyl, the alkenyl and alkynyl radicals preferably being defined as mentioned above individually;

phenyl which is unsubstituted or mono- or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, such as, for example, 2-fluorophenyl, 3-chlorophenyl, 4-bromophenyl, 2-methylphenyl, 3-nitrophenyl, 4-cyanophenyl, 2-trifluoromethylphenyl, 3-methoxyphenyl, 4-trifluoroethoxyphenyl, 2-methylthiophenyl, 2,4-dichlorophenyl, 2-methoxy-3-methylphenyl, 2,4-dimethoxyphenyl, 2-nitro-5-cyanophenyl, 2,6-difluorophenyl;

di-$C_1$–$C_4$-alkylamino, such as, in particular, dimethylamino, dipropylamino, N-propyl-N-methylamino, N-propyl-N-ethylamino, diisopropylamino, N-isopropyl-N-methylamino, N-isopropyl-N-ethylamino, N-isopropyl-N-propylamino;

$R^6$ and $R^7$ are furthermore phenyl which can be substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, as mentioned above individually;

or $R^6$ and $R^7$ together form a cyclized, substituted or unsubstituted $C_4$–$C_7$-alkylene chain which can contain a hetero atom selected from the group consisting of oxygen, sulfur and nitrogen, such as —$(CH_2)_4$—, —$(CH_2)_5$—, —$(CH_2)_6$—, —$(CH_2)_7$—, —$(CH_2)_2$—O—$(CH_2)_2$—, —$CH_2$—S—$(CH_2)_3$—, —$(CH_2)_2$—O—$(CH_2)_3$—, —NH—$(CH_2)_3$—, —$CH_2$—NH—$(CH_2)_2$—, —$CH_2$—CH=CH—$CH_2$—, —CH=CH—$(CH_2)_3$—, suitable substituents being, in particular, $C_1$–$C_4$-alkyl radicals;

e) $R^1$ is furthermore a group

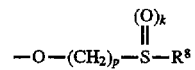

in which k assumes the values 0, 1 and 2, p assumes the values 1, 2, 3 and 4 and $R^8$ is $C_1$–$C_4$-alkyl, $C_1$–$C_4$-haloalkyl, $C_3$–$C_6$-alkenyl, $C_3$–$C_6$-alkynyl or substituted or unsubstituted phenyl, such as mentioned in particular for $R^6$ and $R^7$;

f) $R^1$ is furthermore a radical $OR^9$ where $R^9$ is:

i) hydrogen, the cation of an alkali metal or the cation of an alkaline earth metal, such as lithium, sodium, potassium, calcium, magnesium and barium, or an environmentally compatible organic ammonium ion, such as tert-$C_1$–$C_4$-alkylammonium, or ammonium [$NH_4^+$];

ii) $C_3$–$C_8$-cycloalkyl as mentioned above which can have attached to it one to three $C_1$–$C_4$-alkyl groups;

iii) $C_1$–$C_8$-alkyl, such as, in particular, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, which can have attached to it one to five halogen atoms, in particular fluorine and chlorine, and/or one of the following radicals:

$C_1$–$C_4$-alkoxy, $C_1$–$C_4$-alkylthio, cyano, $C_1$–$C_4$-alkylcarbonyl, $C_3$–$C_8$-cycloalkyl, $C_1$–$C_4$-alkoxycarbonyl, phenyl, phenyl which is mono- or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio, or phenoxy, as mentioned above in particular;

iv) a $C_1$–$C_4$-alkyl group as mentioned above which can have attached to it one to five, preferably one to three, halogen atoms, in particular fluorine and/or chlorine, and which has attached to it one of the following radicals: a 5-membered heteroaromatic ring which contains one to three nitrogen atoms, or a 5-membered heteroaromatic ring which contains one nitrogen atom and one oxygen or sulfur atom, such as pyrazolyl, imidazolyl, benzimidazolyl, triazolyl, benzotriazolyl, isoxazolyl, oxazolyl, thiazolyl, bonded via a C atom or, if possible, N atom, where the heteroaromatic ring can have attached to it one to four halogen atoms and/or one or two of the following radicals:

nitro, cyano, $C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio. The following may be mentioned in particular: 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benztriazolyl, 3-isopropylisoxazol-5-yl, 3-methylisoxazol-5-yl, oxazol-2-yl, thiazol-2-yl, imidazol-2-yl, 3-ethylisoxazol-5-yl, 3-phenylisoxazol-5-yl, 3-tert-butylisoxazol-5-yl;

v) a $C_2$–$C_6$-alkyl group which has attached to it in the 2-position one of the following radicals: $C_1$–$C_4$-alkoxyimino, $C_3$–$C_6$-alkynyloxyimino, $C_3$–$C_6$-haloalkenyloxyimino or benzyloxyimino;

vi) a $C_3$–$C_6$-alkenyl or $C_3$–$C_6$-alkynyl group, it being possible for these groups, in turn, to have attached to them one to five halogen atoms;

vii) $R^9$ is furthermore a phenyl radical which can have attached to it one to five halogen atoms and/or one to three of the following radicals: nitro, cyano, $C_1$–$C_4$-alkyl, $C_3$–$C_4$-haloalkyl, $C_1$–$C_4$-alkoxy, $C_1$–$C_4$-haloalkoxy and/or $C_1$–$C_4$-alkylthio, as mentioned above in particular;

viii) a 5-membered heteroaromatic ring which is linked via a nitrogen atom and which contains one to three nitrogen atoms, such as pyrazolyl, imidazolyl, benzimidazolyl, triazolyl, benzotriazolyl, preferably bonded via the 1-position, it being possible for the heteroaromatic ring to have attached to it one or two halogen atoms and/or one or two of the following radicals: $C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio. The following may be mentioned in particular: 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl-, 1-benzimidazolyl, 1,2,4-triazol-1-yl, 3-methyl-1,2,4-triazol-1-yl,5-methyl-1,2,4-triazol-1-yl, 1-benzotriazolyl, 3,4-dichloroimidazol-1-yl;

ix) $R^9$ is furthermore a group

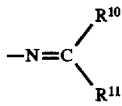

where $R^{10}$ and $R^{11}$ can be identical or different and are:

$C_1$–$C_8$-alkyl, $C_3$–$C_6$-alkenyl, $C_3$–$C_6$-alkynyl, $C_3$–$C_8$-cycloalkyl, it being possible for these radicals to have attached to them a $C_1$–$C_4$-alkoxy, $C_1$–$C_4$-alkylthio and/or substituted or unsubstituted phenyl radical, as mentioned above in particular;

phenyl which can be substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, these radicals corresponding in particular to those mentioned above for $R^1$;

or $R^{10}$ and $R^{11}$ together form a $C_3$–$C_{12}$-alkylene chain which can have attached to it one to three $C_1$–$C_4$-alkyl groups and one hetero atom selected from the group consisting of oxygen, sulfur and nitrogen, as mentioned in particular under $R^6$ and $R^7$;

g) $R^1$ is furthermore a radical —NH—SO$_2$—$R^{12}$ where $R^{12}$ is:

$C_1$–$C_4$-alkyl, $C_3$–$C_6$-alkenyl, $C_3$–$C_6$-alkynyl, $C_3$–$C_8$-cycloalkyl, as mentioned above in particular for $R^1$, it being possible for these radicals to have attached to them a $C_1$–$C_4$-alkoxy, $C_1$–$C_4$-alkylthio and/or a phenyl radical as mentioned above;

substituted or unsubstituted phenyl, in particular as mentioned above.

With a view to the biological action, preferred 3-halo-3-hetarylcarboxylic acid derivatives of the formula I are those in which the remaining substituents have the following meanings:

$R^2$ is a $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio group or a halogen atom as mentioned individually under $R^1$, in particular chlorine, methyl, methoxy, ethoxy, difluoromethoxy, trifluoromethoxy, particularly preferably methoxy;

X is nitrogen or $CR^{13}$, where $R^{13}$ is preferably hydrogen or together with $R^3$ forms a 4- or 5-membered alkylene or alkenylene chain in which in each case one methylene group is replaced by oxygen, such as —CH$_2$—CH$_2$—O—, —CH=CH—O—, —CH$_2$—CH$_2$—CH$_2$O—, —CH=CH—CH$_2$O—, in particular hydrogen and —CH$_2$—CH$_2$O—;

$R^3$ is a $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio group or a halogen atom as mentioned under $R^1$, in particular chlorine, methyl, methoxy, ethoxy, difluoromethoxy, trifluoromethoxy, particularly preferably methoxy, or is linked with $R^{13}$ as mentioned above to form a 5- or 6-membered ring;

$R^4$ is a 5- or 6-membered heteroaryl, such as furyl, thienyl, pyrrolyl, pyrazolyl, imidazolyl, triazolyl, isoxazolyl, oxazolyl, isothiazolyl, thiazolyl,. thiadiazolyl, pyridyl, pyrimidinyl, pyrazinyl, pyridazinyl, triazinyl, for example 2-furyl, 3-furyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 4-pyrrolyl, 3-pyrazolyl, 4-pyrazolyl, 5-pyrazolyl, 2-pyridyl, 3-pyridyl, 4-pyridyl, oxa-2,4-diazolyl, oxa-3,4-diazolyl, thia-2,4-diazolyl, thia-3,4-diazolyl and triazolyl, it being possible for the heteroaromatic rings to have attached to them one or more of the following radicals:

halogen, nitro, cyano, hydroxyl, mercapto, amino, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-alkylamino, di-$C_1$–$C_4$-alkylamino, $C_1$–$C_4$-alkylcarbonyl, $C_1$–$C_4$-alkoxycarbonyl and phenyl, as mentioned above in general and in particular;

$R^5$ is hydrogen, $C_1$–$C_4$-alkyl, $C_3$–$C_6$-alkenyl, $C_3$–$C_6$-alkynyl, $C_3$–$C_8$-cycloalkyl, $C_1$–$C_4$-haloalkyl, $C_1$–$C_4$-alkoxyalkyl, $C_1$–$C_4$-alkylthioalkyl or phenyl, as mentioned above;

Y is sulfur, oxygen or a single bond; and

Z is halogen.

Preferred compounds I are those where $R^5$ is methyl, X is CH, and $R^2$ and $R^3$ are methoxy. Furthermore compounds I where $R^5$ is methyl, X is CH, Z is fluorine and $R^2$ and $R^3$ are methoxy. In addition, $R^1$ is preferably a group $OR^9$, in particular OH and $OC_1$–$C_4$-alkyl.

The variable Y is preferably sulfur and, in particular, oxygen.

Particularly preferred compounds of the formula I are listed in Table I which follows. The definitions of $R^4$ given in this Table and in Tables 1 and 2 are also to be regarded as being preferred, independently of the other definitions of radicals.

TABLE I

| R¹ | R⁴ | R⁵ | R² | R³ | X | Y | Z |
|---|---|---|---|---|---|---|---|
| OH | 2-thienyl | $CH_3$ | $OCH_3$ | $OCH_3$ | CH | S | F |
| OH | 2-thienyl | H | $OCH_3$ | $OCH_3$ | CH | S | F |
| OH | 2-thienyl | $CH_3$ | $OCH_3$ | $OCH_3$ | CH | O | F |
| OH | 2-thienyl | H | $OCH_3$ | $OCH_3$ | CH | O | F |
| OH | 3-thienyl | $CH_3$ | $OCH_3$ | $OCH_3$ | CH | O | F |
| $OCH_3$ | 3-fluoro-2-thienyl | $CH_3$ | $OCH_3$ | $OCH_3$ | CH | O | F |
| $OC_2H_5$ | 2-chloro-3-thienyl | $CH_3$ | $OCH_3$ | $OCH_3$ | N | O | Cl |
| $ON(CH_3)_2$ | 2-furyl | $CH_3$ | $CF_3$ | $CF_3$ | CH | S | Br |
| $ON=C(CH_3)_2$ | 4-bromo-2-furyl | $CH_3$ | $OCF_3$ | $OCF_3$ | CH | O | F |
| $NHSO_2C_6H_5$ | 3-furyl | $CH_3$ | $CH_3$ | $CH_3$ | CH | O | F |
| $NHC_6H_5$ | 4-nitro-3-furyl | $CH_3$ | Cl | Cl | CH | O | Cl |
| ONa | 2-pyrrolyl | $CH_3$ | $OCH_3$ | —$OCH_2$—$CH_2$— | | S | Br |
| $OCH_2$—C≡CH | 5-cyano-2-pyrrolyl | $CH_3$ | $OCH_3$ | $CF_3$ | CH | O | F |
| OH | 3-pyrrolyl | $CH_3$ | $OCH_3$ | $OCF_3$ | CH | O | F |
| $OCH_3$ | 5-methyl-3-pyrrolyl | $CH_3$ | $OCH_3$ | $CH_3$ | CH | O | F |
| $OC_2H_5$ | 3-pyrazolyl | $CH_3$ | $OCH_3$ | Cl | CH | S | Cl |
| $ON(CH_3)_2$ | 4-pyrazolyl | $CH_3$ | $OCH_3$ | $OCH_3$ | CH | O | Cl |
| $ON=C(CH_3)_2$ | 5-pyrazolyl | $CH_3$ | $OCH_3$ | $OCH_3$ | CH | O | Br |
| $NHSO_2C_6H_5$ | 2-imidazolyl | $CH_3$ | $OCH_3$ | $OCH_3$ | CH | O | Br |
| $NHC_6H_5$ | 4-imidazolyl | $CH_3$ | $CF_3$ | $CF_3$ | N | S | F |
| ONa | 1-ethyl-5-imidazolyl | $CH_3$ | $OCF_3$ | $OCF_3$ | N | O | F |
| O—$CH_2$—C≡CH | 3-isoxazolyl | $CH_3$ | $CH_3$ | $CH_3$ | N | O | F |
| OH | 4-isoxazolyl | $CH_3$ | Cl | Cl | N | O | F |
| $OCH_3$ | 5-isoxazolyl | $CH_3$ | $OCH_3$ | —O—$CH_2$—$CH_2$— | | O | Cl |
| $OC_2H_5$ | 2-oxazolyl | $CH_3$ | $OCH_3$ | $CF_3$ | N | S | Br |
| $ON(CH_3)_2$ | 4-oxazolyl | $CH_3$ | $OCH_3$ | $OCF_3$ | N | O | Cl |
| $ON(CH_3)_2$ | 5-oxazolyl | $CH_3$ | $OCH_3$ | $CH_3$ | N | O | Br |
| $NHSO_2C_6H_5$ | 3-isothiazolyl | $CH_3$ | $OCH_3$ | Cl | N | O | F |
| $NHC_6H_5$ | 4-isothiazolyl | $CH_3$ | $OCH_3$ | $OCH_3$ | CH | S | F |
| ONa | 5-isothiazolyl | $CH_3$ | $OCH_3$ | $OCH_3$ | CH | S | F |
| O—$CH_2$—C≡CH | 2-thiazolyl | $CH_3$ | $OCH_3$ | $OCH_3$ | N | S | F |
| OH | 4-thiazolyl | $CH_3$ | $CF_3$ | $CF_3$ | CH | O | F |
| $OCH_3$ | 5-thiazolyl | $CH_3$ | $OCF_3$ | $OCF_3$ | CH | O | Br |
| $OC_2H_5$ | 1,2,3-triazol-4-yl | $CH_3$ | $CH_3$ | $CH_3$ | CH | O | Br |
| $ON(CH_3)_2$ | 2-pyrimidinyl | $CH_3$ | Cl | Cl | CH | O | Cl |
| $ON(CH_3)_2$ | 4-pyrimidinyl | $CH_3$ | $OCH_3$ | —O—$CH_2$—$CH_2$— | | S | F |
| $NHSO_2C_6H_5$ | 5-pyrimidinyl | $CH_3$ | $OCH_3$ | $CF_3$ | N | S | F |
| $NHC_6H_5$ | 2-pyridyl | $CH_3$ | $OCH_3$ | $OCF_3$ | N | S | F |
| ONa | 3-methoxy-2-pyridyl | $CH_3$ | $OCH_3$ | $CH_3$ | N | O | F |
| O—$CH_2$—C≡CH | 4-methylthio-2-pyridyl | $CH_3$ | $OCH_3$ | Cl | N | O | F |
| $OCH_3$ | 5-trifluormethyl-2-pyridyl | $CH_3$ | $OCH_3$ | —O—$CH_2$—$CH_2$— | | O | Cl |
| $OC_2H_5$ | 3-pyridyl | $CH_3$ | $OCH_3$ | $CF_3$ | N | S | Br |
| $ON(CH_3)_2$ | 2-hydroxy-3-pyridyl | $CH_3$ | $OCH_3$ | $OCF_3$ | N | O | F |
| $ON(CH_3)_2$ | 4-dimethylamino-3-pyridyl | $CH_3$ | $OCH_3$ | $CH_3$ | N | O | F |
| $NHSO_2C_6H_5$ | 5-mercapto-3-pyridyl | $CH_3$ | $OCH_3$ | Cl | N | O | F |
| $NHC_6H_5$ | 4-pyridyl | $CH_3$ | $OCH_3$ | $OCH_3$ | CH | S | F |
| ONa | 2-phenyl-4-pyridyl | $CH_3$ | $OCH_3$ | $OCH_3$ | CH | S | Cl |
| O—$CH_2$—C≡CH | 3-methoxycarbonyl-4-pyridyl | $CH_3$ | $OCH_3$ | $OCH_3$ | N | S | Cl |
| OH | 2,6-dimethyl-3-pyridyl | $CH_3$ | $CF_3$ | $CF_3$ | CH | O | F |
| $OCH_3$ | 2,4-dihydroxy-3-pyridyl | $CH_3$ | $OCF_3$ | $OCF_3$ | CH | O | Br |
| $OC_2H_5$ | 2,6-diisopropyl-4-pyridyl | $CH_3$ | $CH_3$ | $CH_3$ | CH | O | F |
| $ON(CH_3)_2$ | oxa-2,4-diazolyl | $CH_3$ | Cl | Cl | CH | O | F |
| $ON=(CH_3)_2$ | thia-3,4-diazolyl | $CH_3$ | $OCH_3$ | —O—$CH_2$—$CH_2$— | | S | Cl |
| $NHSO_2C_6H_5$ | 1,2,4-triazol-2-yl | $CH_3$ | $OCH_3$ | $CF_3$ | N | S | F |
| $NHC_6H_5$ | tetrazolyl | $CH_3$ | $OCH_3$ | $OCF_3$ | N | S | F |
| ONa | oxa-3,4-diazolyl | $CH_3$ | $OCH_3$ | $CH_3$ | N | O | F |
| O—$CH_2$—C≡CH | thia-2,4-diazolyl | $CH_3$ | $OCH_3$ | Cl | N | O | F |

The compounds I, or the herbicidal compositions comprising them, and their environmentally compatible salts, for example salts of alkali metals and alkaline earth metals, are capable of effecting very good control of broad-leaved weeds and grass weeds in crops such as wheat, rice, maize, soya beans and cotton without damaging the crop plants, an effect which is particularly pronounced even at low rates of application. They can be applied, for example, in the form of ready-to-spray solutions, powders, suspensions, also high-percentage aqueous, oily or other suspensions or dispersions, emulsions, oil dispersions, pastes, dusts, spreading materials or granules by means of spraying, atomizing, dusting, scattering or pouring. The use forms depend on the intended purposes; in any case, they should guarantee the finest possible distribution of the active ingredients according to the invention.

The compounds I are generally suitable for the preparation of ready-to-spray solutions, emulsions, pastes or oil dispersions. Suitable inert additives are, inter alia, mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous use forms can be prepared from emulsion concentrates, dispersions, pastes, wettable powders or water-dispersible granules by adding water. To prepare emulsions, pastes or oil dispersions, the substances, as such or dissolved in an oil or solvent, can be homogenized in water by means of a wetting agent, tackifier, dispersant or emulsifier. Alternatively, concentrates composed of active ingredient, wetting agent, tackifier, dispersant or emulsifier and, if desired, solvent or oil may be prepared which are suitable for dilution with water.

Suitable surfactants are the alkali metal salts, alkaline earth metal salts or ammonium salts of aromatic sulfonic acids, for example lignosulfonic acid, phenolsulfonic acid, naphthalenesulfonic acid and dibutylnaphthalenesulfonic acid, and also of fatty acids, alkyl- and alkylarylsulfonates, alkyl sulfates, lauryl ether sulfates and fatty alcohol sulfates, and also salts of sulfated hexa-, hepta- and octadecanols, and also of fatty alcohol glycol ethers, condensation products of sulfonated naphthalene and its derivatives with formaldehyde, condensation products of naphthalene or of naphthalenesulfonic acids with phenol and formaldehyde, polyoxyethylene octyl phenol ether, ethoxylated isooctylphenol, octylphenol or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, spreading materials and dusts can be prepared by mixing or concomitantly grinding the active ingredients with a solid carrier.

Granules, for example coated granules, impregnated granules and homogeneous granules, can be prepared by binding the active ingredients to solid carriers. Solid carriers are mineral earths such as silicic acids, silica gels, silicates, talc, kaolin, limestone, lime, chalk, bole, loess, clay, dolomite, diatomaceous earth, calcium sulfate, magnesium sulfate, magnesium oxide, ground synthetic substances, fertilizers, such as ammonium sulfate, ammonium phosphate, ammonium nitrate, ureas, and plant products, such as cereal meal, or ground tree bark, wood or nutshells, cellulose powder, or other solid carriers.

In general, the formulations comprise from 0.01 to 95% by weight, preferably from 0.5 to 90% by weight, of active ingredient. The active ingredients are employed in a purity of from 90 to 100%, preferably 95 to 100% (according to NMR spectrum).

The compounds I according to the invention can be formulated for example as follows:

I. 20 parts by weight of Compound No. 2.17 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely dispersing it therein gives an aqueous dispersion comprising 0.02% by weight of the active ingredient.

II. 20 parts by weight of Compound No. 2.1 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely dispersing it therein gives an aqueous dispersion comprising 0.02% by weight of the active ingredient.

III. 20 parts by weight of active ingredient No. 2.17 are dissolved in a mixture composed of 25 parts by weight of cyclohexanone, 65 parts by weight of a mineral oil fraction of boiling point 210° to 280° C. and 10 parts by weight of the adduct of 40 mol of ethylene oxide to 1 mol of castor oil. Pouring the solution into 100,000 parts by weight of water and finely dispersing it therein gives an aqueous dispersion comprising 0.02% by weight of the active ingredient.

IV. 20 parts by weight of active ingredient No. 2.2 are mixed thoroughly with 3 parts by weight of sodium diisobutylnaphthalene-a-sulfonate, 17 parts by weight of sodium lignosulfonate from a sulfite waste liquor and 60 parts by weight of pulverulent silica gel, and the mixture is ground in a hammer mill. Finely dispersing the mixture in 20,000 parts by weight of water gives a spray mixture which comprises 0.1% by weight of the active ingredient.

V. 3 parts by weight of active ingredient No. 2.17 are mixed with 97 parts by weight of finely divided kaolin. This gives a dust which comprises 3% by weight of the active ingredient.

VI. 20 parts by weight of active ingredient No. 2.17 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

Application may be effected pre- or post-emergence. If the active ingredients are less well tolerated by certain crop plants, application techniques may be used in which the herbicidal compositions are sprayed, with the aid of the spraying equipment, in such a manner that they come into as little contact as possible with the leaves of the sensitive crop plants, while the active ingredients reach the leaves of undesirable plants growing underneath, or the naked soil surface (post-directed, lay-by).

The rates of application of active ingredient are 0.001 to 5 kg/ha, preferably 0.01 to 2 kg/ha, of active ingredient, depending on the intended aim, the season, the target plants and the growth stage.

Taking into consideration the versatility of the application methods, the compounds according to the invention, or compositions comprising them, can also be employed in a number of other crop plants for eliminating undesirable plants. Suitable crops are, for example, those which follow:

*Allium cepa, Ananas comosus, Arachis hypogaea, Asparagus officinalis, Beta vulgaris* ssp. *altissima, Beta vulgaris* ssp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum* (*N. rustica*), *Olea europaea, oryza sativa, Phaseolus lunatus, Phaseolus vulgaris, Picea abies, Pinus* spp., *Pisum sativum, Prunus avium, Prunus persica,*

*Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera, Zea mays.*

The compounds of the formula I are capable of affecting virtually all development stages of a plant in different ways and are therefore employed as growth regulators. The versatile action of plant growth regulators depends mainly on a) the plant species and cultiva,
b) the timing of application, relative to the development stage of the plant and the season,
c) the site and method of application (for example seed treatment, soil treatment, foliar application or injection to the stem of trees),
d) climatic factors, for example temperature, amount of precipitation, also day length and light intensity,
e) the constitution of the soil (including fertilization),
f) the formulation or use form of the active ingredient and, finally,
g) the concentration of active ingredient applied.

Amongst the various potential uses of plant growth regulators of the formula I in plant cultivation, in agriculture and in horticulture, some are mentioned below.

A. The compounds which can be used according to the invention can be employed for strongly inhibiting the vegetative growth of the plants, which results, in particular, in a reduced longitudinal growth.

Accordingly, the treated plants are distinguished by stunted growth; moreover, the color of the foliage is darker.

An advantage for use in practice is the reduced growth intensity of grasses and crops which are prone to lodging, such as cereals, maize, sunflowers and soya beans. Due to shortened and strengthened stems, the danger of "lodging" (bending over) of plants under adverse weather conditions prior to harvest is reduced or averted.

Another important aspect is the use of growth regulators for inhibiting the longitudinal growth and for altering the maturation in the course of time in cotton. This allows fully mechanized harvesting of this important crop plant.

In fruit trees and other trees, the use of growth regulators saves on pruning costs. Moreover, biennial bearing of fruit trees can be prevented by means of growth regulators.

By using growth regulators, it is also possible to increase, or inhibit, lateral branching of the plants. This is of interest if the formation of lateral shoots (suckers) is to be inhibited in order to favor leaf growth, for example in the case of tobacco plants.

In winter oilseed rape, for example, the resistance to frost may also be increased considerably by using growth regulators. On the one hand, longitudinal growth and the development of too luxuriant a foliage or plant biomass (which is therefore particularly sensitive to frost) is inhibited, and, on the other hand, vegetative growth of the rape plantlets after sowing and before arrival of the winter frosts is retarded despite favorable growth conditions. This also eliminates the danger of frost in such plants, which tend to prematurely break down floral inhibition and switch over to the generative phase. In the case of other crops too, for example winter cereals, it is advantageous for the stand to be well into the tillering phase in autumn by means of treatment with the compounds according to the invention, but not to develop too much the luxuriant growth when winter arrives. All this prevents increased sensitivity to frost and—due to the relatively small quantity of foliage or plant biomass—infection with a variety of diseases (for example fungal diseases).

B. Growth regulators allow increased yields to be obtained, both of parts of plants and of plant constituents. For example, it is possible to induce the growth of larger amounts of buds, flowers, leaves, fruits, seed kernels, roots and tubers, to increase the sugar content in sugar beet, sugar cane and citrus fruits, to increase the protein contents in cereals or soya beans, or to stimulate rubber trees to an increased flow of latex.

The compounds of the formula I can cause higher yields by engaging in the plant metabolism or by enhancing or inhibiting vegetative and/or generative growth.

C. Finally, plant growth regulators allow the development stages to be either shortened or extended, and maturation of the harvested parts of plants to be accelerated or delayed pre- or post-harvest.

An aspect which is of economic interest is, for example, facilitating harvesting, which is made possible by concentrating in the course of time the detachment of, or the reduction of the force required to detach, the fruit from the tree in citrus fruits, olives or in different species and cultivas of pome fruit, stone fruit and hard-shelled fruit. The same mechanism, i.e. promotion of abscission tissue formation between fruit, or leaf, and shoot of the plant is also important for the well controlled defoliage of crop plants such as, for example, cotton.

D. Moreover, the use of growth regulators allows the water consumption of plants to be reduced. By using the substances according to the invention, the intensity of irrigation can be reduced, which makes for more economical management, since, inter alia, the degree of stomatal opening is reduced,
a thicker epidermis and cuticula are formed,
root penetration of the soil is improved, and
the microclimate in the plant stand is affected favorably by more compact growth.

Compounds I are particularly suitable for reducing the length of stems in crop plants such as barley, oilseed rape and wheat.

The active ingredients of the formula I to be used according to the invention can be applied to the crop plants either via the seed (in the form of a seed treatment product) or via the soil, i.e. via the root, and, particularly preferably, via the leaf, by means of spraying.

The rate of application of active ingredient is not critical since it is extremely well tolerated by plants. The optimum application rate varies, depending on the intended purpose, the season, the target plants and the growth stages.

In the case of seed treatment, amounts of active ingredient of from 0.001 to 50 g, preferably 0.01 to 10 g, are generally required per kilogram of seed.

In the case of foliar and soil treatment, rates of 0.001 to 10 kg/ha, preferably 0.01 to 3 kg/ha, in particular 0.01 to 0.5 kg/ha, are generally considered as sufficient.

To broaden the spectrum of action and to achieve synergistic effects, the compounds of the formula I can be mixed with a large number of representatives of other groups of herbicidal or growth-regulating active ingredients and then applied together. Suitable components for mixtures are, for example, diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which have attached to them in the 2-position for example a carboxyl or carbimino group, quinolinecarboxylic acid derivatives, imidazolinones, sulfonamides, sulfonylureas, aryloxy- or heteroaryloxyphenoxypropionic acids and their salts, esters and amides, and others.

Moreover, it can be advantageous to apply the compounds of the formula I, alone or in combination with other herbicides, additionally in the form of a mixture with other crop protection agents, for example pesticides or agents for controlling phytopathogenic fungi or bacteria. The miscibility with mineral salt solutions which are employed for remedying nutritional and trace element deficiencies is furthermore of interest. Non-phytotoxic oils and oil concentrates can additionally be added.

SYNTHESIS EXMAPLES

Synthesis of compounds of the general formula VI

Example 1

Methyl 3-fluoro-3-(2-thienyl)-2-hydroxybutyrate 19.5 g (100 mmol) of methyl 3-(2-thienyl)-2,3-epoxybutyrate are dissolved in 50 ml of dried dichloromethane, and this is added dropwise to a solution of 100 ml of hydrogen fluoride/pyridine complex (70% of HF) in 100 ml of dried dichloromethane. After 1 hour at room temperature, the reaction solution is stirred into 150 ml of ice-water. The organic phase is washed using bicarbonate solution and water, dried over magnesium sulfate and concentrated. The residue is recrystallized from petroleum ether with the addition of a small amount of ethyl acetate.

Yield: 17.2 g (79%).

Example 2

Methyl 3-chloro-3-(3-pyridyl)-2-hydroxybutyrate 0.8 g (20 mmol) of LiCl is dissolved in 100 ml of absolute tetrahydrofuran (THF), the solution is cooled to −20° C., and 20 ml of titanium tetrachloride (1M in dichloromethane) are added dropwise. After the mixture has been stirred for 30 minutes at −20° C., it is cooled to −78° C., and 3.8 g (20 mmol) of methyl 3-(3-pyridyl)-2,3-epoxybutyrate in 50 ml of THF are added dropwise. After the mixture has warmed to room temperature, stirring is continued for 6 hours, the solvent is distilled off, and the residue partitioned between ethyl acetate and water.

The aqueous phase is extracted using ethyl acetate, and the combined organic phases are dried over sodium sulfate and concentrated. The residue is purified further by chromatography on silica gel using n-hexane/ethyl acetate mixtures. After the solvent has been distilled off, 2.9 g of a pale yellow oil remain.

Yield: 63%.

All compounds mentioned in Table 1 were prepared in a similar manner.

TABLE 1

Intermediates of the formula VI where $R^1 = OCH_3$

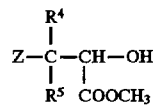

| No. | $R^4$ | $R^5$ | Z | Diastereomers M.p. [°C.] |
|---|---|---|---|---|
| 1.1 | 2-thienyl | $CH_3$ | F | 1:1 |
| 1.2 | 3-pyridyl | $CH_3$ | Cl | 2:1 |
| 1.3 | 2-thienyl | H | F | |
| 1.4 | 3-thienyl | $CH_3$ | F | |
| 1.5 | 3-thienyl | H | F | |
| 1.6 | 2-furyl | $CH_3$ | F | |
| 1.7 | 2-furyl | H | F | |
| 1.8 | 3-furyl | $CH_3$ | F | |
| 1.9 | 3-furyl | H | F | |
| 1.10 | 2-pyridyl | $CH_3$ | F | |
| 1.11 | 3-pyridyl | $CH_3$ | F | |
| 1.12 | 4-pyridyl | $CH_3$ | F | |
| 1.13 | 2-thiazolyl | $CH_3$ | F | |
| 1.14 | 2-pyrrolyl | $CH_3$ | F | |
| 1.15 | 3-isoxazolyl | $CH_3$ | F | |
| 1.16 | 1-methyl-2-pyrrolyl | $CH_3$ | F | |
| 1.17 | 3-methyl-2-thienyl | $CH_3$ | F | |
| 1.18 | 1-methyl-3-pyrrolyl | $CH_3$ | F | |
| 1.19 | 5-methyl-2-furyl | $CH_3$ | F | |
| 1.20 | 2,5-dimethyl-2-thienyl | $CH_3$ | F | |

Synthesis of compounds of the general formula I:

Example 3

Methyl 3-(2-thienyl)-3-fluoro-2-[(4,6-dimethoxypyrimidin-2-yl)oxy]butyrate 2.2 g (10 mmol) of methyl 3-(2-thienyl)-3-fluoro-2-hydroxybutyrate (Compound 1.1) are dissolved in 40 ml of dimethylformamide, and 0.3 g (12 mmol) of sodium hydride is added. The mixture is stirred for 1 hour, and 2.2 g (10 mmol) of 4,6-dimethoxy-2-methylsulfonylpyrimidine are then added. After the mixture has been stirred at room temperature for 24 hours, it is hydrolyzed using 10 ml of water, the pH is brought to 5 using acetic acid, and the solvent is distilled off under a high vacuum. The residue is taken up in ethyl acetate, washed with water and dried over sodium sulfate, and the solvent is distilled off. The residue is treated with 10 ml of methyl t-butyl ether and the precipitate formed filtered off with suction. After drying, 1.8 g of a white powder remain.

Yield: 61% (diastereomer mixture 1:1).

Example 4

3-(2-Thienyl)-3-fluoro-2-[(4,6-dimethoxypyrimidin-2-yl)oxy]-butyric acid 0.9 g (3 mmol) of methyl 3-(2-thienyl)-3-fluoro-2-(4,6-dimethoxypyrimidin-2-yl)oxybutyrate (from Ex. 3) are dissolved in 20 ml of methanol and 20 ml of tetrahydrofuran, and 3.7 g of 10% strength NaOH solution are added. The mixture is stirred for 6 hours at 60° C. and for 12 hours at room temperature, the solvents are distilled off in vacuo, and the residue is taken up in 100 ml of water. The aqueous phase is now extracted using ethyl acetate and subsequently brought to pH 1-2 using dilute hydrochloric acid and extracted using ethyl acetate. After the mixture has been dried over magnesium sulfate and the solvent distilled off, a small amount of acetone is added to the residue and the precipitate which has formed is filtered off with suction. After drying, 0.8 g of a white powder remains.

Yield: 89% (diastereomer mixture 3:2)

Example 5

Methyl 3-(2-thienyl)-3-fluoro-2-[(4 6-dimethoxypyrimidin-2-yl)thio]butyrate 5.5 g (25 mmol) of methyl 3-(2-thienyl)-3-fluoro-2-hydroxybutyrate (Compound 1.1) are dissolved in 50 ml of dichloromethane, 3 g (30 mmol) of triethylamine are added, and 3.2 g (28 mmol) of methanesulfonyl chloride are added dropwise with stirring. The mixture is stirred for 2 hours at room temperature, washed with water, dried over magnesium sulfate and concentrated in vacuo. The residue is taken up in dimethylformamide (DMF), and this is added dropwise at 0° C. to a suspension of 12.9 g (75 mmol) of 4,6-dimethoxypyrimidine-2-thiol and 8.4 g (100 mmol) of sodium hydrogen carbonate in 100 ml of DMF. After the mixture has been stirred for 2 hours at room temperature and for a further 2 hours at 60° C., the mixture is poured into 1 l of ice-water, and the precipitate which has formed is filtered off with suction. After drying, 2.5 g of a white powder remain.

Yield: 31% (diastereomer mixture 1:1).

The compounds mentioned in Table 2 were prepared analogously to the above Examples.

TABLE 2

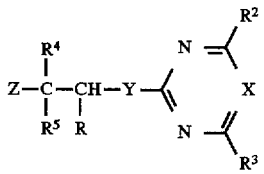

| No. | $R^4$ | Z | $R^5$ | Y | $R^1$ | DR* | M.p. [°C.] |
|---|---|---|---|---|---|---|---|
| 2.1 | 2-thienyl | F | $CH_3$ | O | $OCH_3$ | 1:1 | |
| 2.2 | 2-thienyl | F | $CH_3$ | O | OH | 3:2 | |
| 2.3 | 2-thienyl | F | $CH_3$ | S | $OCH_3$ | 1:1 | |
| 2.4 | 2-thienyl | F | $CH_3$ | S | OH | | |
| 2.5 | 2-thienyl | F | H | O | $OCH_3$ | | |
| 2.6 | 2-thienyl | F | H | O | OH | | |
| 2.7 | 3-thienyl | F | $CH_3$ | O | $OCH_3$ | | |
| 2.8 | 3-thienyl | F | $CH_3$ | O | OH | | |
| 2.9 | 3-thienyl | F | H | O | $OCH_3$ | | |
| 2.10 | 3-thienyl | F | H | O | OH | | |
| 2.11 | 2-furyl | F | $CH_3$ | O | $OCH_3$ | | |
| 2.12 | 2-furyl | F | $CH_3$ | O | OH | | |
| 2.13 | 3-furyl | F | $CH_3$ | O | $OCH_3$ | | |
| 2.14 | 3-furyl | F | $CH_3$ | O | OH | | |
| 2.15 | 2-pyridyl | F | $CH_3$ | O | $OCH_3$ | | |
| 2.16 | 2-pyridyl | F | $CH_3$ | O | OH | | |
| 2.17 | 3-pyridyl | F | $CH_3$ | O | $OCH_3$ | 3:1 | 154–156 |
| 2.18 | 3-pyridyl | F | $CH_3$ | O | OH | | |
| 2.19 | 4-pyridyl | F | $CH_3$ | O | $OCH_3$ | | |
| 2.20 | 4-pyridyl | F | $CH_3$ | O | OH | | |

*diastereomeric ratio

Use Examples

The herbicidal action of the 3-(het)arylcarboxylic acid derivatives of the general formula I was demonstrated by greenhouse experiments:

The culture vessels used were plastic flowerpots containing loamy sand with about 3.0% of humus as the substrate. The seeds of the test plants were sown separately for each species.

In the case of pre-emergence treatment, the active ingredients were suspended or emulsified in water and applied by means of finely distributing nozzles directly after sowing. The vessels were irrigated slightly to promote germination and growth and subsequently covered with translucent plastic hoods until the plants had rooted. This cover causes uniform germination of the test plants unless this has been adversely affected by the active ingredients.

For post-emergence treatment, the test plants are first grown until they have reached a height of 3 to 15 cm, depending on the growth form, and only then treated with the active ingredients which had been suspended or emulsified in water. To this end, the test plants are either sown directly and grown in the same containers, or they are first grown separately as seedlings and transplanted into the test containers a few days prior to treatment.

Depending on the species, the plants were kept at from 10° to 25° C., or 20° to 35° C. The test period extended over 2 to 4 weeks. During this time, the plants were tended, and their response to the individual treatments was evaluated.

Evaluation was carried out using a scale from 0 to 100. 100 means no emergence of the plants or complete destruction of at least the aerial parts, and 0 means no damage or normal course of growth.

We claim:

1. A 3-halo-3-hetarylcarboxylic acid compound of the formula I

in which R is a group $$\underset{\|}{\overset{O}{C}}-R^1$$

in which $R^1$ has the following meanings:

a) hydrogen;

b) a succinylimidoxy group;

c) a 5-membered heteroaromatic ring which is linked via a nitrogen atom, which contains two or three nitrogen atoms, and which can have attached to it one or two halogen atoms and/or one or two of the following radicals:

$C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

d) a radical —$(O)_m$—$NR^6R^7$,
in which m is 0 or 1 and $R^6$ and $R^7$ can be identical or different and have the following meanings: hydrogen;

$C_1$–$C_8$-alkyl, $C_3$–$C_6$-alkenyl, $C_3$–$C_6$-alkynyl, $C_3$–$C_8$-cycloalkyl, it being possible for these radicals to have attached to them in each case one to five halogen atoms and/or one or two of the following groups:

$C_1$–$C_4$-alkoxy, $C_3$–$C_6$-alkenyloxy, $C_3$–$C_6$-alkynyloxy, $C_1$–$C_4$-alkylthio, $C_3$–$C_6$-alkenylthio, $C_3$–$C_6$-alkynylthio, $C_1$–$C_4$-haloalkoxy, $C_1$–$C_4$-alkylcarbonyl, $C_3$–$C_6$-alkenylcarbonyl, $C_3$–$C_6$-alkynylcarbonyl, $C_1$–$C_4$-alkoxycarbonyl, $C_3$–$C_6$-alkenyloxycarbonyl, $C_3$–$C_6$-alkynyloxycarbonyl, di-$C_1$–$C_4$-alkylamino, $C_3$–$C_8$-cycloalkyl, phenyl, or phenyl which is mono- or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

phenyl which can be substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

$R^6$ and $R^7$ together are a cyclized, substituted or unsubstituted $C_4$–$C_7$-alkylene chain or together are a cyclized, substituted or unsubstituted $C_3$–$C_6$-alkylene chain having one hetero atom selected from the group consisting of oxygen, sulfur or nitrogen;

e) $R^1$ is furthermore a group

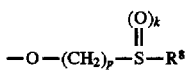

in which $R^8$ is $C_1$–$C_4$-alkyl, phenyl, phenyl which is mono- or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, or $C_1$–$C_4$-haloalkyl, $C_3$–$C_6$-alkenyl or $C_3$–$C_6$-alkynyl, p assumes the values 1, 2, 3 or 4 and k assumes the values 0, 1 or 2;

f) a radical $OR^9$ where $R^9$ is:

i) hydrogen, an alkali metal cation, the equivalent of an alkaline earth metal cation, the ammonium cation or an organic ammonium ion;

ii) a $C_3$–$C_8$-cycloalkyl group which can have attached to it one to three $C_1$–$C_4$-alkyl radicals;

iii) a $C_1$–$C_8$-alkyl group which can have attached to it one to five halogen atoms and/or one of the following radicals:
$C_1$–$C_4$-alkoxy, $C_1$–$C_4$-alkylthio, cyano, $C_1$–$C_4$-alkylcarbonyl, $C_3$–$C_8$-cycloalkyl, $C_1$–$C_4$-alkoxycarbonyl, phenyl, phenyl which is mono- or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio, or phenoxy;

iv) a $C_1$–$C_8$-alkyl group which can have attached to it one to five halogen atoms and which has attached to it one of the following radicals: a 5-membered heteroaromatic ring which contains one to three nitrogen atoms, or a 5-membered heteroaromatic ring which contains one nitrogen atom and one oxygen or sulfur atom, it being possible for the heteroaromatic rings to have attached to them one to four halogen atoms and/or one or two of the following radicals: nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

v) a $C_2$–$C_6$-alkyl group which has attached to it in the 2-position one of the following radicals: $C_1$–$C_4$-alkoxyimino, $C_3$–$C_6$-alkenyloxyimino, $C_3$–$C_6$-haloalkenyloxyimino or benzyloxyimino;

vi) a $C_3$–$C_6$-alkenyl or $C_3$–$C_6$-alkynyl group, it being possible for these groups, in turn, to have attached to them one to five halogen atoms;

vii) a phenyl radical which can have attached to it one to five halogen atoms and/or one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

viii) a 5-membered heteroaromatic ring which is linked via a nitrogen atom, which contains one to three nitrogen atoms, and which can have attached to it one or two halogen atoms and/or one or two of the following radicals: nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

ix) $R^9$ is furthermore a group

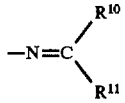

where $R^{10}$ and $R^{11}$ are identical or different and are: $C_1$–$C_8$-alkyl, $C_3$–$C_6$-alkenyl, $C_3$–$C_6$-alkynyl, $C_3$–$C_8$-cycloalkyl, it being possible for these radicals to have attached to them a $C_1$–$C_4$-alkoxy, $C_1$–$C_4$-alkylthio and/or phenyl radical;

phenyl which can be substituted by one or more of the following radicals:
halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

or $R^{10}$ and $R^{11}$ together form a $C_3$–$C_{12}$-alkylene chain which can have attached to it one to three $C_1$–$C_4$-alkyl groups;

g) or $R^1$ forms a radical —NH—$SO_2$—$R^{12}$ where $R^{12}$ is: $C_1$–$C_4$-alkyl, $C_3$–$C_6$-alkenyl, $C_3$–$C_6$-alkynyl, $C_3$–$C_8$-cycloalkyl, it being possible for these radicals to have attached to them a $C_1$–$C_4$-alkoxy, $C_1$–$C_4$-alkylthio and/or a phenyl radical;

phenyl which can be substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, and the remaining substituents have the following meanings:

$R^2$ is halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

X is $CR^{13}$, where $R^{13}$ is hydrogen or together with $R^3$ forms a 3- to 4-membered alkylene or alkenylene chain in which in each case one methylene group is replaced by oxygen;

$R^3$ is halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, or $R^3$ is linked to $R^{13}$ as mentioned above to form a 5- or 6-membered ring;

$R^4$ is a five- or six-membered heteroaromatic ring which contains one to three nitrogen atoms and/or one sulfur or oxygen atom and which can have attached to it one or more of the following radicals: halogen, nitro, cyano, hydroxyl, mercapto, amino, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino, di-$C_1$–$C_4$-alkylamino, $C_1$–$C_4$-alkylcarbonyl, $C_1$–$C_4$-alkoxycarbonyl or phenyl;

$R^5$ is hydrogen, $C_1$–$C_4$-alkyl, $C_3$–$C_6$-alkenyl, $C_3$–$C_6$-alkynyl, $C_3$–$C_8$-cycloalkyl, $C_1$–$C_4$-haloalkyl, $C_1$–$C_4$-alkoxyalkyl, $C_1$–$C_4$-alkylthioalkyl or phenyl;

Y is sulfur or oxygen or a single bond; and

Z is halogen.

2. A 3-halo-3-hetarylcarboxylic acid derivative of the formula I as defined in claim 1, where $R^5$ is methyl, X is CH, $R^2$ and $R^3$ are methoxy and Y, Z, $R^1$ and $R^4$ have the meanings given in claim 1.

3. A 3-halo-3-hetarylcarboxylic acid derivative of the formula I as defined in claim 1, where Z is fluorine, $R^5$ is methyl, X is CH, $R^2$ and $R^3$ are methoxy and Y, $R^1$ and $R^4$ have the meanings given in claim 1.

4. A herbicidal composition comprising a compound of the formula I as defined in claim 1 and inert carrier.

5. A method of controlling undesired plant growth, which comprises allowing a herbicidally effective amount of a compound of the formula I as defined in claim 1 to act on the plants or their environment.

6. A composition for reducing the stem length in crop plants, comprising a compound of the formula I as defined in claim 1 and inert carrier.

7. A method of regulating the growth of plants, which comprises allowing a growth regulating amount of a compound of the formula I as defined in claim 1 to act on the plants or their environment.

8. A halo-3-hetarylcarboxylic acid derivative of the formula VI

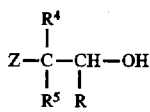
VI in which R, $R^4$, $R^5$ and Z have the meanings given in claim 1.

9. A process for the preparation of 3-hetarylcarboxylic acid derivatives of the formula VI

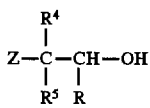
VI which comprises reacting epoxides of the general formula IV

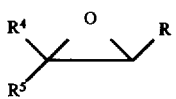
IV where R, $R^4$ and $R^5$ have the meanings given in claim 1 with compounds of the general formula V

MZ      V where Z is halogen and M is an alkali metal cation, the equivalent of an alkaline earth metal cation or hydrogen, in the presence or absence of an inert solvent and/or in the presence of a suitable catalyst.

10. A process for the preparation of 3-halo-3-hetarylcarboxylic acid derivatives of the formula I as defined in claim 1, where Y is oxygen, which comprises reacting 3-halo-3-hetarylcarboxylic acid derivatives of the formula VI

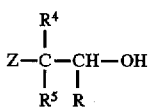
VI where the substituents have the meanings given in claim 1, with compounds of the general formula VII

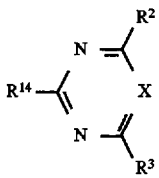
VII where $R^{14}$ is halogen or $R^{15}SO_2$—, $R^{15}$ being $C_1$-$C_4$-alkyl, $C_1$-$C_4$-haloalkyl or phenyl, in an inert solvent in the presence of a base.

11. A process for the preparation of 3-halo-3-hetarylcarboxylic acid derivatives of the formula I as defined in claim 1, where Y is sulfur, which comprises reacting 3-halo-3-hetarylcarboxylic acid derivatives of the formula VIII

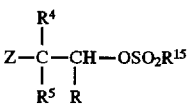
VIII where the substituents have the meanings given in claim 10, with compounds of the general formula IX

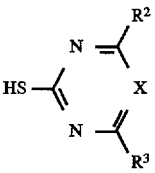
IX where $R^2$, $R^3$ and X have the meanings given in claim 1.

* * * * *